(12) United States Patent
Zeng et al.

(10) Patent No.: US 10,869,878 B2
(45) Date of Patent: Dec. 22, 2020

(54) VAGINAL COMPOSITION AND USE THEREOF

(71) Applicant: SINGAPORE ZE&Z INTERNATIONAL PTE. LTD, Singapore (SG)

(72) Inventors: Zhongming Zeng, Guangdong (CN); Ruyun Zhou, Guangdong (CN)

(73) Assignee: SINGAPORE ZE&Z INTERNATIONAL PTE. LTD, Singapore (SG)

( * ) Notice: Subject to any disclaimer, the term of this patent is extended or adjusted under 35 U.S.C. 154(b) by 918 days.

(21) Appl. No.: 15/262,529

(22) Filed: Sep. 12, 2016

(65) Prior Publication Data

US 2016/0375045 A1 Dec. 29, 2016

Related U.S. Application Data

(63) Continuation of application No. PCT/CN2015/073978, filed on Mar. 11, 2015.

(30) Foreign Application Priority Data

Mar. 13, 2014 (CN) .......................... 2014 1 0103662

(51) Int. Cl.
| | | |
|---|---|---|
| *A61K 31/7016* | (2006.01) | |
| *A61K 31/565* | (2006.01) | |
| *A61K 9/00* | (2006.01) | |
| *A61K 9/06* | (2006.01) | |
| *A61K 36/886* | (2006.01) | |

(52) U.S. Cl.
CPC ........ *A61K 31/7016* (2013.01); *A61K 9/0034* (2013.01); *A61K 9/06* (2013.01); *A61K 31/565* (2013.01); *A61K 36/886* (2013.01)

(58) Field of Classification Search
CPC ...................................................... A61K 36/00
USPC ......................................................... 424/725
See application file for complete search history.

(56) References Cited

U.S. PATENT DOCUMENTS

| | | | |
|---|---|---|---|
| 3,860,707 A | | 1/1975 | Wootton |
| 2004/0170708 A1* | | 9/2004 | Thompson ........... A61K 31/045 |
| | | | 424/757 |
| 2007/0264309 A1* | | 11/2007 | Chollet ................ A61K 9/0034 |
| | | | 424/433 |

FOREIGN PATENT DOCUMENTS

| | | | | |
|---|---|---|---|---|
| CN | 102123736 | | 7/2011 | |
| CN | 102123736 A | * | 7/2011 | ........... A61K 9/0034 |
| WO | 9926635 | | 6/1999 | |
| WO | WO-9926635 A1 | * | 6/1999 | ........ A61K 31/7004 |
| WO | WO-2011041938 A1 | * | 4/2011 | ........... A61K 31/715 |

OTHER PUBLICATIONS

Lina et al, "Embryotoxicity/Teratogenicity Study with Isomaltulose (Palatinose ®) in Rats", Food and Chemical Toxicology 35 (1997) 309-314 (Year: 1997).*
International Search Report filed in PCT/CN2015/073978 dated Jun. 11, 2015.

* cited by examiner

*Primary Examiner* — Michael Barker
*Assistant Examiner* — Deborah A Davis
(74) *Attorney, Agent, or Firm* — Rankin, Hill & Clark LLP

(57) ABSTRACT

A use of isomaltulose in the preparation of a vaginal composition, wherein the amount of isomaltulose used is 0.05-20% (w/w). A vaginal composition contains 0.05-20% (w/w) of isomaltulose. The composition may be a health product, health care product, cleaning product, skin care product, deodorant, cosmetic, or disinfectant composition or a pharmaceutical composition. A non-therapeutic vaginal care method, a non-therapeutic vaginal cleaning method, a method for improving vaginal acidity, a method for promoting growth of *Lactobacillus* in the vagina, and a method for preventing and treating vaginal dysbacteriosis, especially bacterial vaginal diseases, these methods being implemented by administering the composition to women's vagina.

9 Claims, No Drawings

VAGINAL COMPOSITION AND USE THEREOF

TECHNICAL FIELD

The present invention relates to the use of isomaltulose in the preparation of a vaginal composition. The present invention also relates to a vaginal composition, which may be a health product, a health care product, a cleaning product, a nursing product, a deodorant, a cosmetic, a disinfectant composition, or a pharmaceutical composition. In particular, the present invention further relates to a non-therapeutic vaginal care and nursing method, a non-therapeutic vaginal cleaning method, a method for enhancing vaginal acidity, a method for promoting the growth of protective *Lactobacilli* in the vagina, and a method for preventing and treating vaginal dysbacteriosis, especially bacterial vaginosis.

BACKGROUND

Female vagina is an open system that is vulnerable to the invasion of a variety of microorganisms and pathogens. In healthy state, beneficial *Lactobacilli* reside on the surface of vaginal mucosa. *Lactobacilli* can metabolize glycogen in the vaginal mucosal epithelial cells to produce acids. Thus the vaginal acidity is kept within the range of pH 3.5 to 4.5, which plays an important role in vaginal self-cleaning and in vaginal anti-infection resistance. Once the acidity of the vagina is reduced, the healthy condition of vagina and upper genital tract would be impaired, and women would suffer from adverse health outcomes.

There are numerous *Lactobacillus* species present in the vagina, and almost twenty species have been detected[1]. Before 2000, *Lactobacillus acidophilus* was believed to be the dominant *Lactobacillus* species. Since 2000, with the development and wide use of molecular identification technologies, a breakthrough has been made in the research of *Lactobacillus* species present in the vagina. Zhou (2004), Linhares (2010), and Rampersaud R (2012)[2][3][4] reported that preponderant microflora of the *Lactobacilli* in the vagina were *L. crispatus*, or *L. iners* and *L. gasseri*, or *L. jensenii*, or may be *L. gallinarum* and *L. vaginalis*. They also reported that *Lactobacilli* were not the dominant bacteria in the vagina of all the "healthy" women. Rather, *Atopobium* was the dominant in some women, which could also produce lactic acid to maintain the weakly acidic environment of the vagina.

In addition to *Lactobacilli*, many other kinds of bacteria also reside in the vagina of healthy women. Fredricks et al (2005)[5] reported that *Escherichia coli, Peptostreptococcus, Finegoldia, Prevotella, Anaerococcus, Lactobacilli reuteri, Streptococcus, Allisonella, Lachnospiraceae, Moryella, Aerococcus, Gardnerella, Mobiluncus, Sneathia, Peptomphilus* and the like were detected in the vagina of healthy women.

Especially when the vaginal acidity is reduced, beneficial *Lactobacilli* decline, and complex species of anaerobic bacteria and aerobic/facultative aerobic bacteria, e.g., *Staphylococcus, Escherichia coli*, et al, grow massiviely, which may result in negative outcomes to women's health, jeopardizing the quality of life, and causing diseases such as bacterial vaginosis (BV) in serious cases.

Menstruation, sexual intercourse and vaginal douche, etc, have a great impact on the vaginal acidity. For example, the vaginal acidity is reduced in the first week after menstruation, when the vaginal pH value is remarkably higher than 4.5 and may be as high as 6.6[6]. The seminal fluid can reduce the vaginal acidity significantly[7]. Therefore, after menstruation and after sexual intercourse, vaginal douche is an option for the personal hygiene, aesthetic, and high quality life of women and for the prevention of infection. About 30% of the American women frequently undertake vaginal douche. However, improper douche will destroy the vaginal acidity and bacterial flora, which increases the chance of vaginal infection[8].

For example, the vaginal acidity is reduced in BV patients, and the vaginal pH value may rise to 4.5 or higher, so as that the *Lactobacilli* in the vagina decline, and various anaerobic bacteria grow massively. Fredricks et al (2005)[5] reported that by analyzing bacterial flora using 16S-rDNA sequencing technology in the vagina of BV patients, an average of 9-17 types of anaerobic bacteria were detected per patient, including *Megasphaera* and *Sneathia*. Livengood et al (2009)[9] reported that *Gardnerella vaginalis* was detected in the vaginal secretions of almost every BV patients, *Atopobium vaginae* was detected in the vaginal secretions of nearly 95% of the BV patients, and *Mobiluncus* spp was detected in the vaginal secretions of nearly 50% of the BV patients. Many other anaerobic bacteria, for example *Prevotella* and anaerobic *Streptococcus*, etc, are also important BV bacteria.

The cure criteria for BV treatment include the vaginal acidity being returned to normal, that is, the vaginal pH value returns to the range of 3.5-4.5. Internationally, the preferred therapies for BV are primarily anti-bacterial agent metronidazole which has potent effect on anaerobic bacteria, and secondarily clindamycin and other anti-bacterial agents. However, the cure rate of these two agents is only about 60%, the recurrence rate is as high as 30-40%, and the cure rate decreases gradually. Livengood C H et al (2007)[10] reported that according to the guideline issued by FDA in 1998, when both the clinical and microbiological cure standards were met, the cure rate of tinidazole for BV was only 37%. The cure rate is 57%, according to the standard that a cure is achieved if 3 of the 4 traditional Amsel clinical criteria are normal. Thomas K K et al (2005)[11] reported that the cure rate of a 0.75% metronidazole gel for BV was only 26%.

In view of the openness, vulnerability, and susceptibility of the woman's vagina, and the difficulty of traditional vaginal douche, antibacterial agents and products in meeting the needs for routine hygiene, nourishing and health care of the woman's vagina, and especially in meeting the needs for vaginal hygiene, vaginal nourishing and health care after menstruation, sexual intercourse, menopause, vaginal infection and other special physiological and pathological conditions, there is an urgent need for developing an effective vaginal health product, health care product, hygiene product as well as medicine to maintain the health and guarantee the quality of women's life.

SUMMARY

The objective of the present invention is to provide a vaginal use product composition, and the use of the composition in non-therapeutic routine vaginal health care, routine vaginal nourishing, routine vaginal wetting, routine vaginal lubrication, or routine vaginal cleaning, so as to increase the comfort and freshness of the vagina and vulva; particularly in non-therapeutic vaginal health care, vaginal nourishing, vaginal lubrication, wetting, or cleaning after menstruation, sexual intercourse, menopause, vaginal douche, vaginal treatment with an agent, or vaginal infection, to enhance the self-purification of the vagina or increase the resistance of the vagina to pathogens; in increasing the vaginal acidity, keeping the vaginal acidity within a pH range of 3.5 to 4.5, or promoting the growth of protective *Lactobacilli*, particularly *L. crispatus, L. jensenii* or *L. gasseri* in the vagina; also particularly in eliminating or alleviating odor of vaginal secretions, eliminating or alleviating vaginal and vulvar pruritus, eliminating or alleviating vaginal and vulvar dryness, eliminating or alleviating vaginal and vulvar soreness, painful intercourse and other discomforts, or improving the characteristics of leucorrhea; and in modulating the vaginal bacterial flora, in restoring the beneficial vaginal bacterial flora after antibacterial treatment, in preventing or treating vaginal dysbacteriosis, or in preventing or treating bacterial vaginosis.

Research suggests that four most common *Lactobacilli* including *L. crispatus, L. jensenii, L. gasseri* and *L. iners* play different roles in maintaining the normal physiology and stability of the vaginal bacterial flora. Ma et al (2012)[12] reported a study regarding the stability of the vaginal bacterial flora, wherein compared with the vaginal bacterial floras having other three *Lactobacilli* as preponderant flora, the vaginal bacterial flora having *L. iners* as preponderant flora were unstable and susceptible to change. This may be correlated with the weak $H_2O_2$ producing capability of *L. iners*. Antonio et al[13] found that among the *Lactobacilli* isolated from female vagina, only 9% of the *L. iners* strain can produce $H_2O_2$, while 95% of the *L. crispatus* strain, 94% of the *L. jensenii* strain, and 71% of the *L. gasseri* strain can produce $H_2O_2$. It can be seen that only when *L. crispatus, L. jensenii*, or *L. gasseri* is restored to be preponderant vaginal flora, is it most favorable for the vaginal bacterial flora to maintain a normal and stable state. Therefore, these three species of *Lactobacillus* are also referred to as "protective *Lactobacilli*" in the vagina.

In view of the openness, vulnerability and susceptibility of the woman's vagina, and the difficulty of traditional vaginal douche and antibacterial agents and products in meeting the needs of vaginal cleaning, nourishing and health care of women after menstruation, sexual intercourse, menopause, vaginal infection and other special physiological and pathological conditions, the inventors have carried out a lot of studies and tests, and find that isomaltulose has a potent vaginal acidity enhancing effect, and can strongly promote the growth of 3 protective *Lactobacilli*, including *L. crispatus, L. jensenii*, and *L. gasseri*. The isomaltulose can significantly enhance the self-purification and anti-infection resistance of vagina, and it is particularly suitable for the preparation of non-therapeutic vaginal health products, daily use commodities, health care products, cosmetics, hygiene products, cleaning products, or nourishing products, and also suitable for the preparation of therapeutic vaginal health products, medicines, or medical devices. On this basis, the present invention is accomplished through further researches.

The present invention provides the use of isomaltulose in the preparation of a vaginal composition, wherein in the preparation process, the isomaltulose is used in such an amount that the composition contains 0.05 to 20% (w/w) of isomaltulose, and preferably used in such an amount that the composition contains 1.5 to 12% (w/w) of isomaltulose.

The use of isomaltulose, in the preparation of a composition according to the present invention, the composition further contains 0.05-2.5% (w/w) in total of one or more preservatives and/or antibacterial agents selected from the group consisting of benzoic acid, sodium benzoate, sorbic acid, potassium sorbate, sodium sorbate, acetic acid, sodium acetate, diacetic acid, sodium diacetate, dehydoacetic acid, sodium dehydroacetate, propionic acid, sodium propionate, calcium propionate, caprylic acid, sodium caprylate, capric acid, sodium caprate, undecylenic acid, sodium undecylenate, lauric acid, sodium laurate, chitosan, oligochitosan, natamycin, lactoferrin and lactoferricin, and the combination thereof.

The preservatives and/or antibacterial agents have a high inhibitive effect on the growth of pathogenic bacteria, molds and *Candida*, while have a relatively weak inhibitive effect on *Lactobacillus*. When applied for the preparing of vaginal composition according to the present invention, the preservatives and/or antibacterial agents can not only retard the growth of pathogenic bacteria, molds and *Candida*, but also avoid significant interference and weakening on the promoting effect of isomaltulose on the growth and acid production of *Lactobacillus*.

The use of isomaltulose, in the preparation of a composition according to the present invention, inactive adjuvant/matrix ingredients are also used. The choices of the preparation process, method and adjuvant are those predictable by those skilled in the art based on the disclosure of the present invention concerning their skills and background knowledge.

According to the use of isomaltulose, in the preparation of a composition according to the present invention, wherein the use is: applying the isomaltulose into preparation of vaginal composition products or composition formulations including, but not limited to, non-therapeutic vaginal health products, vaginal use commodities, vaginal health care products, vaginal care products, vaginal cosmetics, vaginal hygiene products, or vaginal cleaning products; therapeutic vaginal health products, vaginal medical devices, or vaginal medicines (nonprescription medicines or prescription medicines); vaginal cleaning agents or nourishing agents, deodorants, antipruritic agents, fresheners, wetting agents, lubricating agents, disinfectants, antibacterial agents, topical microbicidal agents, microecological modulators, or microorganism regulating agents.

The use of isomaltulose in the preparation of a composition according to the present invention, wherein the use is: applying the isomaltulose into preparation of vaginal compositions in dosage forms including, but not limited to, water-soluble gels, aqueous solutions, aerosols, creams, ointments, capsules, microcapsules, suppositories, effervescents, tablets and preferably water-soluble gels and creams.

For example, when preparing the water-soluble vaginal gel composition, it can be prepared following a method known to those skilled in the art as follows, quantitatively weigh and uniformly mix isomaltulose, sodium benzoate, sodium propionate, sodium dehydroacetate, and a water-soluble gel matrix (e.g. xanthan gum), quantitatively add distilled water, and stir until the carbohydrate and preservatives are dissolved, and the water-soluble gel matrix swells as an uniform viscous gel. The composition is adjusted to a pH range of 3.5-6.0 and particularly a pH range of 4.0-5.5 with a pharmaceutically acceptable acid and/or base. The composition is packaged and then sterilized, or sterilized and then aseptically packaged. The sterilization may be radiation sterilization, high-temperature sterilization at 110-115° C. for 15-20 min, intermittent sterilization, or sterilization by filtering the solutions formulated with the preservative and carbohydrate ingredients respectively, and then add them to a sterilized water-soluble gelatineous matrix.

When preparing the vaginal tablets, they can be prepared following a method known to those skilled in the art as follows, quantitatively weigh and uniformly mix isomaltulose with sodium benzoate, sodium propionate, and sodium dehydroacetate and then directly tablet to obtain tablets. During the process, auxiliary ingredients, for example, a lubricating agent such as magnesium stearate or a disintegrant such as sodium carboxymethyl starch, may also be added, uniformly mixed, and then tabletted.

The vaginal suppository may be prepared following a method known to those skilled in the art as follows, quantitatively weigh and uniformly mix and grind isomaltulose, sodium benzoate, sodium propionate, sodium dehydroacetate, and Tween 80, and heating to about 50° C.; additionally heat mixed fatty acid glyceride (also referred to as solid fat) to 60° C. to melt it; then add the mixed solution of the carbohydrate, preservatives and Tween 80 to the melted matrix with stirring; and after being fully mixed, pouring the mixture to a mold at about 40° C. (i.e. prior to solidification), slightly cooling, then sweeping the mold, cooling and releasing from the mold, to obtain a vaginal suppository. The matrix for suppositories may be, in addition to mixed fatty acid glyceride, propylene stearate, glycerogelatin and Tween-61 etc. Moreover, an automated mechanical device may be used for mass production.

The use of isomaltulose, in the preparation of a composition according to the present invention, an effective amount of one or more antibacterial agents and/or preservatives may be further optionally employed to prepare the composition, including, but not limited to, hydrogen peroxide, vitamin $B_1$, vitamin $K_3$, vitamin $K_4$, a p-hydroxybenzoate, defensins and antibacterial peptides. These substances can further inhibit the bacteria, molds and *Candida* in the composition, thus further enhancing the microbial stability of the composition.

The use of isomaltulose in the preparation of a vaginal composition according to the present invention, 0.001-1.0% (w/w) in total of one or more estrogens and/or phytoestrogens may be optionally used to prepare the composition, wherein the estrogens and phytoestrogens include, but not limited to, stilboestrol, estradiol, estriol, daidzin, daidzein, genistin, genistein, glycitin, glycitein, biochanin A, coumestrol, formononetin. The estrogens and phytoestrogens can facilitate vaginal mucosal angiogenesis, vaginal mucosal epithelial keratinization and vaginal epithelial wound healing, thereby enhancing the efficacy of the composition prepared in the present invention. The choice and use of the estrogens and phytoestrogens in the preparation of the composition according to the present invention are within the scope of knowledge of those skilled in the art.

The use of isomaltulose, in the preparation of a composition according to the present invention, one or more vaginal mucosal cell protectants and/or antioxidants may be optionally used to prepare the composition, which are selected from the group consisting of, without limitation, 0.1-5.0% (w/w) of aloe extract, 0.1-5.0 (w/w) of lavender extract, 0.001-1.0% (w/w) of vitamin E, 0.001-1.0% (w/w) of vitamin A, 0.001-1.0% (w/w) of vitamin D and 0.001-1.0% (w/w) of vitamin C, and used for further nourishing, wetting, lubricating, and protecting the vaginal mucosal epithelial cells.

The use of isomaltulose, in the preparation of a composition according to the present invention, an effective amount of one or more carbohydrates may be optionally used to prepare the composition, which are selected from the group consisting of, without limitation, glucose, fructose, mannose, sucrose, maltose, isomaltose, lactose, lactulose, trehalose, cellobiose, melibiose, gentiobiose, turanose, chitobiose, raffinose, gentianose, panose, melezitose, isomaltotriose, kestose, isomaltotetraose, nystose, fructofuranosylnystose, malto-oligosaccharide, galactooligosaccharide, mannose oligosaccharide, dextran, cyclodextrin, dextrin, starch, and glycogen.

The use of isomaltulose, in the preparation of a composition according to the present invention, one or more antimicrobial agents effective for bacteria and/or fungi may be optionally used to prepare the composition, including, but not limited to, fluconazole, terconazole, butoconazole, miconazole, clotrimazole, nystatin, metronidazole, tinidazole, lincomycin and amoxicillin. The bacteriostats and/or fungicides are preferably metronidazole, tinidazole, clotrimazole and fluconazole. The choice and use of the bacteriostats and/or fungicides in the preparation of the composition according to the present invention are within the scope of knowledge of those ordinarily skilled in the art.

The use of isomaltulose, in the preparation of a composition according to the present invention, wherein a water-soluble gel is prepared, the content of isomaltulose is 0.1-20.0% (w/v) and preferably 3.0-12.0% (w/v) in total.

The use of isomaltulose, in the preparation of a composition according to the present invention, a non-flowable, viscous water-soluble gel matrix is used in the preparation of a water-soluble gel, which allows the carbohydrate to contact the vaginal mucosa evenly and reside for a long period of time, thus exerting an effect of promoting the growth of *Lactobacilli*. The choice and use of the viscous water-soluble gel matrix are within the scope of knowledge of those skilled in the art. In the use of isomaltulose in the preparation of the composition according to the present invention, the matrix includes, but is not limited to, xanthan gum and Carbomer.

The use of isomaltulose, in the preparation of a composition according to the present invention, wherein a water-soluble gel is prepared, the pH value is adjusted to the range of 3.5-6.0, and particularly to the range of 4.0-5.5. The choices of the kinds and concentration of the acid or base for adjusting the pH value of the water-soluble gel described in the present invention are within the scope of knowledge of those ordinarily skilled in the art.

The water-soluble gel prepared according to the use in preparation provided in the present invention may be packed in an aseptic and sealed package, and preferably in a single-dose aseptic and sealed package. The composition amenable to sterilization or aseptic processing may be packed and sealed in an aseptic package by using the aseptic processing technology familiar to those skilled in the art. Alternatively, the prepared composition is packed, sealed and then sterilized, or the prepared composition is packed in a disposable dispenser, sealed in an external package and sterilized with radiation.

According to a preferred embodiment of the present invention, viable *Lactobacilli* may be optionally used to prepare capsules, microcapsules, tablets and so on, which contain both the isomaltulose and the viable *Lactobacilli*, wherein the viable *Lactobacilli* are used to directly supplement the *Lactobacilli* lacked in the vagina of the patients, or replace the *Lactobacilli* previously existing in the vagina of the patients, and the isomaltulose is used to promote the growth of the *Lactobacilli* in the vagina. The composition containing isomaltulose and viable *Lactobacilli* prepared according to the use of isomaltulose in preparation provided in the present invention is suitable for modulating the vaginal bacterial flora, enhancing the vaginal acidity, cleaning and nursing the vagina and preventing or treating *L. vaginalis* deficiency, weakened vaginal acidity, bacterial vaginosis and vaginal dysbacteriosis. The preparation and use of viable *Lactobacilli* in the composition of the present invention are within the scope of knowledge of those skilled in the art.

The present invention also particularly provides a vaginal composition, comprising (1) 0.05-20% (w/w) of isomaltulose; (2) 0.05-2.5% (w/w) in total of one or more preservatives and/or antibacterial agents selected from the group consisting of: benzoic acid, sodium benzoate, sorbic acid, potassium sorbate, sodium sorbate, acetic acid, sodium acetate, diacetic acid, sodium diacetate, dehydroacetic acid, sodium dehydroacetate, propionic acid, sodium propionate, calcium propionate, caprylic acid, sodium caprylate, capric acid, sodium caprate, undecylenic acid, sodium undecylenate, lauric acid, sodium laurate, chitosan, oligochitosan, natamycin, lactoferrin and lactoferricin; and (3) one or more inactive adjuvant ingredients suitable for use in the vagina of human beings.

In the composition according to the present invention, the content of isomaltulose is preferably 1.5-12% (w/w).

The composition according to the present invention may be a vaginal composition product or composition formulation including, but not limited to, non-therapeutic vaginal health product, vaginal daily use commodity, vaginal health care product, vaginal nursing product, vaginal cosmetic, vaginal hygiene product, or vaginal cleaning product; therapeutic vaginal health product, vaginal medical device, or vaginal medicine (nonprescription medicine or prescription medicine); or vaginal cleaning agent or nourishing agent, deodorant, deodorant, antipruritic agent, freshener, wetting agent, lubricating agent, disinfectant, antibacterial agent, topical microbicidal agent, microecological modulator, or microorganism regulating agent.

The vaginal composition is in the dosage form including, but not limited to, water-soluble gels, aqueous solutions, aerosols, creams, ointments, capsules, microcapsules, suppositories, effervescents, tablets and preferably water-soluble gels and creams.

The composition according to the present invention may further optionally contain an effective amount of one or more preservatives and/or antibacterial agents selected from the group consisting of, without limitation, hydrogen peroxide, vitamin $B_1$, vitamin $K_3$, vitamin $K_4$, p-hydroxybenzoate, defensins and antibacterial peptides. These substances can further inhibit the bacteria, molds and *Candida* in the composition, thus further enhancing the microbial stability of the composition.

The composition according to the present invention may further optionally contain 0.001-1.0% (w/w) in total of one or more estrogens and/or phytoestrogens, including, but not limited to, stilboestrol, estradiol, estriol, daidzin, daidzein, genistin, genistein, glycitin, glycitein, biochanin A, coumestrol, formononetin and so on. The estrogens and phytoestrogens can facilitate vaginal mucosal angiogenesis, vaginal mucosal epithelial keratinization and vaginal epithelial wound healing, thereby further enhancing the efficacy of the composition prepared in the present invention. The choice and use of the estrogens and phytoestrogens in the composition of the present invention are disclosed and within the scope of knowledge of those skilled in the art.

The composition according to the present invention may further optionally contain an effective amount of one or more vaginal mucosal cell protectants and/or antioxidants selected from the group consisting of, without limitation, 0.1-5.0% (w/w) of aloe extract, 0.1-5.0 (w/w) of lavender extract, 0.001-1.0% (w/w) of vitamin E, 0.001-1.0% (w/w) of vitamin A, 0.001-1.0% (w/w) of vitamin D and 0.001-1.0% (w/w) of vitamin C, for further nourishing, wetting, lubricating and protecting the vaginal mucosal epithelial cells. The choice and use of the materials above in the composition of the present invention are disclosed and within the scope of knowledge of those skilled in the art.

The composition according to the present invention may further optionally contain an effective amount of one or more carbohydrates selected from the group consisting of, without limitation, glucose, fructose, mannose, sucrose, maltose, isomaltose, lactose, lactulose, trehalose, cellobiose, melibiose, gentiobiose, turanose, chitobiose, raffinose, gentianose, panose, melezitose, isomaltotriose, kestose, isomaltotetraose, nystose, fructofuranosylnystose, malto-oligosaccharide, galactooligosaccharide, mannose oligosaccharide, dextran, cyclodextrin, dextrin, starch and glycogen. The choice and use of the carbohydrates above in the composition of the present invention are disclosed and within the scope of knowledge of those skilled in the art.

The composition according to the present invention may further optionally contain an effective amount of one or more antimicrobial agents selected from the group consisting of, without limitation, fluconazole, terconazole, butoconazole, miconazole, clotrimazole, nystatin, metronidazole, tinidazole, lincomycin and amoxycillin, and preferably metronidazole, tinidazole, fluconazole and clotrimazole.

The composition according to the present invention may further optionally contain viable *Lactobacilli*, including, but not limited to, *L. crispatus, L. jensenii* and *L. gasseri*. The viable *Lactobacilli* are used to directly supplement the *Lactobacilli* lacked in the vagina of the patients, or replace the *Lactobacilli* previously existing in the vagina of the patients, and the isomaltulose is used to promote the growth of the *Lactobacilli* in the vagina. Therefore the composition according to the present invention containing isomaltulose and viable *Lactobacilli* is suitable for modulating the vaginal bacterial flora, enhancing the vaginal acidity, cleaning and nursing the vagina, and preventing or treating *L. vaginalis* deficiency, weakened vaginal acidity, bacterial vaginosis and vaginal dysbacteriosis. The preparation and use of viable *Lactobacilli* in the composition of the present invention are disclosed and within the scope of knowledge of those skilled in the art.

The composition according to the present invention is preferably a water-soluble vaginal gel composition. The water-soluble vaginal gel composition comprises (1) 0.1-20.0% (w/v) and preferably 3.0-12.0% (w/v) of isomaltulose; (2) 0.1-2.5% (w/v) in total of one or more preservatives and/or antibacterial agents selected from the group consisting of benzoic acid, sodium benzoate, sorbic acid, potassium sorbate, sodium sorbate, acetic acid, sodium acetate, diacetic acid, sodium diacetate, dehydroacetic acid, sodium dehydroacetate, propionic acid, sodium propionate, calcium propionate, caprylic acid, sodium caprylate, capric acid, sodium caprate, undecylenic acid, sodium undecylenate, lauric acid, sodium laurate, chitosan, oligochitosan, natamycin, lactoferrin and lactoferricin; and (3) an inactive adjuvant ingredient that is a non-flowable, viscous water-soluble gel matrix, wherein the gel matrix is preferably xanthan gum and Carbomer and further preferably xanthan gum. The composition has (4) a pH range of 3.5-6.0, and particularly a pH range of 4.0-5.5. The composition further optionally contains (5) 0.0015-1.0% (w/v) in total of one or more estrogens and/or phytoestrogens selected from the group consisting of stilboestrol, estradiol, estriol, daidzin, daidzein, genistin, genistein, glycitin, glycitein, biochanin A, coumestrol and formononetin; (6) one or more vaginal mucosal cell protectants and/or antioxidants selected from the group consisting of, without limitation, 0.15-5.0% (w/v) of aloe extract, 0.15-5.0% (w/v) of lavender extract, 0.0015-1.0% (w/v) of vitamin E, 0.0015-1.0% (w/v) of vitamin A, 0.0015-1.0% (w/w) of vitamin D and 0.0015-1.0% (w/w) of vitamin C; and (7) bacteriostats and/or fungicides selected from the group consisting of metronidazole, tinidazole, clotrimazole and fluconazole. When the bacteriostat and/or fungicide is metronidazole, the concentration of metronidazole is 0.00015-0.1% (w/v), and preferably 0.0015-0.01% (w/v).

The present invention also particularly relates to a method for supplementing a carbohydrate to a vagina of a woman, comprising administering an effective amount of a vaginal composition containing isomaltulose of the present invention to the vagina of a woman in need thereof. The daily dosage of isomaltulose is 5-2000 mg, and preferably 150-1200 mg, which may be dosed from 1 to 2 times, such that the amount of isomaltulose is not higher than 1000 mg in each administration.

The present invention also particularly relates to a method for non-therapeutic routine vaginal health care, routine vaginal nourishing, routine vaginal wetting, routine vaginal lubrication, or routine vaginal cleaning, so as to increase the comfort and freshness of the vagina and vulva, comprising administering an effective amount of a vaginal composition of the present invention to the vagina of a woman in need thereof. The daily dosage of isomaltulose is 5-2000 mg, and preferably 150-1200 mg, which may be dosed from 1 to 2 times, such that the amount of isomaltulose is not higher than 1000 mg in each administration. Through the method of the present invention, the cleanness, comfort and freshness of the vagina and vulva can be increased or maintained.

The present invention also particularly relates to a method for non-therapeutical vaginal cleaning, vaginal health care, vaginal nourishing, wetting, or lubricating after menstruation, sexual intercourse, menopause, vaginal douche, or vaginal treatment with an agent, to enhance the self-purification of the vagina or increase the resistance of the vagina to pathogens, comprising administering an effective amount of a vaginal composition of the present invention to the vagina of a woman in need thereof. The daily dosage of isomaltulose is 5-2000 mg, and preferably 150-1200 mg, which may be dosed from 1 to 2 times, such that the amount of isomaltulose is not higher than 1000 mg in each administration. Through the method of the present invention, the self-purification of the vagina can be enhanced, or the resistance of the vagina to pathogens can be increased, such that the cleanness, hygiene and health of the vagina are maintained.

The present invention also particularly relates to a method for increasing the vaginal acidity, or keeping the vaginal acidity within a pH range of 3.5-4.5, comprising administering an effective amount of a composition of the present invention to the vagina of a woman in need thereof. The daily dosage of isomaltulose is 5-2000 mg, and preferably 150-1200 mg, which may be dosed from 1 to 2 times, such that the amount of isomaltulose is not higher than 1000 mg in each administration. Through the method of the present invention, the vaginal acidity is increased, or kept within a pH range of 3.5-4.5, and particularly a pH range of 3.8-4.3.

The present invention also particularly relates to a method for promoting the growth of protective *Lactobacilli*, particularly protective *L. crispatus, L. jensenii*, or *L. gasseri* in the vagina, comprising administering an effective amount of a composition of the present invention to the vagina of a woman in need thereof The daily dosage of isomaltulose is 5-2000 mg, and preferably 150-1200 mg, which may be dosed from 1 to 2 times, such that the amount of isomaltulose is not higher than 1000 mg in each administration. Through the method of the present invention, the growth of protective *Lactobacilli*, particularly protective *L. crispatus, L. jensenii*, or *L. gasseri* in the vagina is significantly promoted.

The present invention also particularly relates to a method for eliminating or alleviating odor of vaginal secretions, eliminating or alleviating vaginal and vulvar pruritus, eliminating or alleviating vaginal and vulvar dryness, eliminating or alleviating vaginal and vulvar soreness, painful intercourse and other discomforts, or improving the characteristics of leucorrhea, comprising administering an effective amount of a composition of the present invention to the vagina of a woman in need thereof. The daily dosage of isomaltulose is 5-2000 mg, and preferably 150-1200 mg, which may be dosed from 1 to 2 times, such that the amount of isomaltulose is not higher than 1000 mg in each administration. Through the method of the present invention, the characteristics of leucorrhea are considerably improved, the odor of leucorrhea is eliminated or alleviated, and the vaginal and vulvar pruritus, dryness and soreness are eliminated or alleviated.

The present invention also particularly relates to a method for modulating the vaginal bacterial flora, restoring the beneficial vaginal bacterial flora after anti-bacterial treatment, preventing or treating vaginal dysbacteriosis, or preventing or treating bacterial vaginosis, comprising administering an effective amount of a composition of the present invention to the vagina of a woman in need thereof. The daily dosage of isomaltulose is 5-2000 mg, and preferably 150-1200 mg, which may be dosed from 1 to 2 times, such that the amount of isomaltulose is not higher than 1000 mg in each administration. The present invention is also useful in the modulation of the vaginal bacterial flora, the prevention or treatment of vaginal dysbacteriosis, the restoration of the beneficial vaginal bacterial flora after anti-bacterial treatment, or the prevention or treatment of bacterial vaginosis.

DETAILED DESCRIPTION

Composition Example

Example 1

The composition was prepared with a method as follows: 9.0 g of isomaltulose, 0.05 g of sodium benzoate, 0.02 g of sodium dehydroacetate, 0.5 g of sodium propionate, and 2.7 g of xanthan gum were uniformly mixed. Then 100 ml of distilled water was added to dissolve isomaltulose, sodium benzoate, sodium dehydroacetate and sodium propionate, stirred until uniform, upon which xanthan gum swelled and formed a uniform viscous gel. The gel was adjusted to pH 5.0 and sterilized at 112.6° C. for 20 min, and the water-soluble gel composition of the present invention was obtained. The gel was packed into individual, aseptic and sealed single dose package, 5 g per package.

Example 2

The raw materials were weighed according to the amounts below, and the composition was prepared essentially following the method of Example 1: isomaltulose 4.5 g, sodium dehydroacetate 0.02 g, sodium propionate 0.5 g, natamycin 2.5 mg, xanthan gum 2.6 g, and distilled water 100 ml, pH 5.0. After sterilization, the gel was packed into individual, aseptic and sealed single dose package, 5 g per package.

Example 3

The raw materials were weighed according to the amounts below, and the composition was prepared essentially following the method of Example 1: isomaltulose 12.0 g, sodium benzoate 0.15 g, sodium dehydroacetate 0.01 g, sodium propionate 0.5 g, xanthan gum 2.5 g and distilled water 100 ml, pH 4.8.

Example 4

The raw materials were weighed according to the amounts below, and the composition was prepared essentially following the method of Example 1: isomaltulose 20.0 g, sodium benzoate 0.2 g, xanthan gum 3.0 g and distilled water 100 ml, pH 5.0.

Example 5

The raw materials were weighed according to the amounts below, and the composition was prepared essentially following the method of Example 1: isomaltulose 0.1 g, sodium benzoate 0.2 g, lauric acid 0.1 g, xanthan gum 2.5 g and distilled water 100 ml, pH 6.5.

Example 6

The raw materials were weighed according to the amounts below, and the composition was prepared essentially following the method of Example 1: isomaltulose 8 g, sodium caprate 0.1 g, lactoferrin 1.0 g, aloe extract 5 g, xanthan gum 2.5 g and distilled water 100 ml, pH 6.5.

Example 7

The raw materials were weighed according to the amounts below, and the composition was prepared essentially following the method of Example 1: isomaltulose 1.5 g, sodium propionate 0.375 g, sodium caprylate 0.15 g, lactoferrin 0.25 g, xanthan gum 2.5 g and distilled water 100 ml, pH 6.5.

Example 8

The raw materials were weighed according to the amounts below: isomaltulose 45.0 g, isomaltose 443.5 g, sodium benzoate 1.5 g and *Lactobacillus acidophilus* powder 10 g (containing fructooligosaccharide and $5\times10^{10}$ CFU of viable bacteria). The ingredients above were fully mixed until uniform, and packed into 1000 capsules, each capsule containing 45 mg of isomaltulose, 443.5 mg of isomaltose, 1.5 mg of sodium benzoate and $5\times10^{7}$ CFU of *Lactobacillus acidophilus*.

Example 9

The raw materials were weighed according to the amounts below, and the composition was prepared essentially following the method of Example 1: isomaltulose 9.0 g, sodium propionate 0.45 g, sodium benzoate 0.05 g, sodium dehydroacetate 0.025 g, estriol 0.1 g, xanthan gum 3.0 g and water 87.375 g, pH 5.0.

Example 10

The raw materials were weighed according to the amounts below, and the composition was prepared essentially following the method of Example 1: isomaltulose 10 g, sodium benzoate 0.15 g, natamycin 2 mg, xanthan gum 3.0 g and distilled water 100 ml, pH 5.0.

Example 11

The raw materials were weighed according to the amounts below, and the composition was prepared essentially following the method of Example 1: isomaltulose 5.0 g, sodium benzoate 0.2 g, xanthan gum 2.5 g and distilled water 100 ml, pH 5.5.

Example 12

The raw materials were weighed according to the amounts below, and the composition was prepared essentially following the method of Example 1: isomaltulose 2.0 g, sodium propionate 0.7 g, xanthan gum 2.5 g and distilled water 94.8 g, pH 6.5.

Example 13

The raw materials were weighed according to the amounts below, and the composition was prepared essentially following the method of Example 1: isomaltulose 6.0 g, sodium propionate 0.5 g, sodium dehydroacetate 0.02 g, sodium caprylate 0.05 g, lactoferrin 0.5 g, natamycin 10 mg, total soy isoflavones 0.02 g, xanthan gum 2.5 g and distilled water 100 ml, pH 6.5.

Example 14

The raw materials were weighed according to the amounts below, and the composition was prepared essentially following the method of Example 1: isomaltulose 1.5 g, sodium dehydroacetate 0.025 g, xanthan gum 3.0 g and distilled water 100 ml, pH 6.5.

Example 15

The raw materials were weighed according to the amounts below, and the composition was prepared essentially following the method of Example 1: isomaltulose 8.5 g, sodium dehydroacetate 0.02 g, sodium caprylate 0.1 g, lactoferrin 0.5 g, xanthan gum 2.8 g and distilled water 100 ml, pH 6.5.

Example 16

The raw materials were weighed according to the amounts below, and the composition was prepared essentially following the method of Example 1: isomaltulose 8.0 g, sodium propionate 0.5 g, xanthan gum 2.8 g and distilled water 100 ml, pH 6.2.

Example 17

The raw materials were weighed according to the amounts below, and the composition was prepared essentially following the method of Example 1: isomaltulose 8.0 g, sodium propionate 0.5 g, sodium dehydroacetate 0.02 g, lactoferrin 0.5 g, xanthan gum 2.8 g and distilled water 100 ml, pH 6.2.

Example 18

The raw materials were weighed according to the amounts below, and the composition was prepared essentially following the method of Example 1: isomaltulose 9.0 g, sodium benzoate 0.2 g, fluconazole 0.2 g, xanthan gum 3.0 g and distilled water 100 ml, pH 6.5.

Example 19

The raw materials were weighed according to the amounts below, and the composition was prepared essentially following the method of Example 1: isomaltulose 1.5 g, sodium propionate 0.5 g, sodium dehydroacetate 0.025 g, xanthan gum 2.5 g and distilled water 100 ml, pH 5.4.

Example 20

The raw materials were weighed according to the amounts below: isomaltulose 20.0 g, sodium propionate 0.5 g, sodium benzoate 0.05 g, sodium dehydroacetate 0.02 g, metronidazole 0.005 g, xanthan gum 2.5 g and distilled water 100 ml.

Isomaltulose, sodium propionate, sodium benzoate, sodium dehydroacetate and xanthan gum were uniformly mixed. Then 90 ml of distilled water was added, stirred, stirred and heated, and sterilized. 10 ml of a sterilized metronidazole solution (containing 0.005 g of metronidazole) was added, adjusted to pH 5.0 and uniformly mixed.

Example 21

The raw materials were weighed according to the amounts below: isomaltulose 35 g, isomaltose 63 g, sodium benzoate 0.5 g, metronidazole 0.01 g, clotrimazole 0.01 g, magnesium stearate 1.48 g, uniformly mixed and tabletted. Each tablet weighed 0.5 g and contained 175 mg of isomaltulose, 315 mg of isomaltose, 2.5 mg of sodium benzoate, 0.05 mg of metronidazole, 0.05 mg of clotrimazole and 7.4 mg of magnesium stearate.

Example 22

The raw materials were weighed according to the amounts below, and the composition was prepared essentially following the method of Example 1: isomaltulose 10 g, benzoic acid 0.05 g, Polycarbophil 2.0 g and distilled water 100 ml, pH 4.0.

Example 23

The raw materials were weighed according to the amounts below, and the composition was prepared essentially following the method of Example 1: benzoic acid 0.15 g, isomaltulose 3.0 g, isomaltose 9.0 g, fluconazole 0.15 g, xanthan gum 2.5 g and distilled water 100 g, pH 5.4.

Example 24

An aqueous solution of a composition was prepared according to the amounts and the method below. 12 g of isomaltulose and 0.2 g of sodium benzoate were weighed, added to 100 ml of distilled water, stirred, dissolved, adjusted to pH 5.0 and sterilized, and an aqueous solution of the composition is obtained.

Example 25

An aqueous solution of a composition was prepared according to the amounts and the method below. 12 g of isomaltulose, 0.5 g of sodium propionate, 0.02 g of sodium dehydroacetate, and 0.1 g of sodium caprylate were weighed, added into 100 ml of distilled water, stirred, dissolved, adjusted to pH 5.0 and sterilized.

The benefits of the use of isomaltulose in the preparation and the preparation method provided in the present invention are described below with reference to following experimental examples.

Experimental Example 1

1. Experimental Purpose

To observe the promotion of isomaltulose for acid production by BV-associated bacteria, and compare the promotion effect with that of isomaltose, sucrose and maltose.

2. Experimental Method (1) Grouping in experiment:
① Isomaltulose group: containing 1% (w/v) isomaltulose, MRS basal medium without carbohydrate, 5% (w/v) calf serum, and 0.5% (w/v) xanthan gum, pH5.4;
② Isomaltose group: containing 1% (w/v) isomaltose, MRS basal medium without carbohydrate, 5% (w/v) calf serum, and 0.5% (w/v) xanthan gum, pH5.4;
③ Sucrose group: containing 1% (w/v) sucrose, MRS basal medium without carbohydrate, 5% (w/v) calf serum, and 0.5% (w/v) xanthan gum, pH5.4; and
④ Maltose group: containing 1% (w/v) maltose, MRS basal medium without carbohydrate, 5% (w/v) calf serum, and 0.5% (w/v) xanthan gum, pH5.4.

The gel of each group was formulated essentially following the method described in Composition Example 1, then sterilized, added with calf serum, and packed in test tubes in a specification of 5 g/tube, for late use.

(2) Secretion specimens from BV patients: vaginal secretions from 5 BV patients; and the criteria of inclusion are:
① conforming to the Amsel clinical criteria of BV diagnosis, wherein the pH value of the vaginal secretions was >4.6;
② after smearing, Gram staining and microscopical examination of vaginal secretions, Nugent score ≥7; and
③ no other vaginosis and no antimicrobial agent is used within two weeks.

(3) After sampling, the secretion specimens from BV patients meeting the criteria of inclusion were immediately inoculated to the above 4 gels containing a carbohydrate, and slightly aerobically incubated at 37° C. for 46 hrs. The pH values of the gel matrices are detected with a precise pH test paper respectively at 14 hrs, 36 hrs, and 46 hrs.

3. Experimental Results

As shown in Table 1, the pH in each test tube declines from the initial value 5.4 to a value in the range of 3.8-5.1 after the secretion specimens from BV patients are incubated for 14 hrs in the 4 gels containing a carbohydrate, wherein the pH of the isomaltulose gel is the lowest, the pH of the sucrose gel is the highest and the pH of the isomaltose and maltose gels are in the middle. After 36 hr-incubation, the pH of the 4 gels containing a carbohydrate declines to below 4.6, wherein the pH of the isomaltulose gel is the lowest and the pH of the sucrose gel is the highest. After 46 hr-incubation, the pH values of the 4 gels containing a carbohydrate are the same and ≤3.8.

TABLE 1

Effect of four carbohydrates on acid production by BV-associated bacteria

|  | Isomaltulose | Isomaltose | Sucrose | Maltose |
|---|---|---|---|---|
| 0 hr: | | | | |
| Specimen 1 | 5.4 | 5.4 | 5.4 | 5.4 |
| Specimen 2 | 5.4 | 5.4 | 5.4 | 5.4 |
| Specimen 3 | 5.4 | 5.4 | 5.4 | 5.4 |
| Specimen 4 | 5.4 | 5.4 | 5.4 | 5.4 |
| Specimen 5 | 5.4 | 5.4 | 5.4 | 5.4 |
| 14 hrs | | | | |
| Specimen 1 | ≤3.8 | 3.8 | ≤3.8 | 3.8 |
| Specimen 2 | 4.1 | 4.1-4.4 | 4.4 | 4.1-4.4 |
| Specimen 3 | 3.8-4.1 | 4.1-4.4 | 4.8-5.1 | 4.1-4.4 |
| Specimen 4 | 4.1 | 4.4 | 4.8-5.1 | 4.6 |
| Specimen 5 | 4.1-4.4 | 4.1-4.4 | 4.4-4.6 | 4.1-4.4 |
| 36 hrs: | | | | |
| Specimen 3 | ≤3.8 | ≤3.8 | 4.4-4.6 | ≤3.8 |
| Specimen 4 | ≤3.8 | ≤3.8 | ≤3.8 | ≤3.8 |
| Specimen 5 | ≤3.8 | 4.1-4.4 | 4.4-4.6 | 4.1-4.4 |
| 46 hrs: | | | | |
| Specimen 1 | ≤3.8 | ≤3.8 | ≤3.8 | ≤3.8 |
| Specimen 2 | ≤3.8 | ≤3.8 | ≤3.8 | ≤3.8 |

4. Discussion

In this example, after the carbohydrate containing gels are inoculated with the secretion specimens from BV patients, and slightly aerobically incubated for 14 hrs, the pH values in 4 of 5 isomaltulose gels decline to below 4.1, the pH values in 4 of 5 isomaltose gels and in 4 of 5 maltose gels decline to below 4.4 and the pH values in 4 of 5 sucrose gel are still 4.4 or above.

After continuous incubation for 36 hrs, the pH values in 3 of 3 isomaltulose gels decline to 3.8 or below, the pH values in 2 of 3 sucrose gels are still above 4.4 and the pH values in 2 of 3 isomaltose gels and 2 of 3 maltose gels decline to 3.8 or below.

After continuous incubation for 46 hrs, the pH values in the 4 carbohydrate containing gels inoculated respectively with 2 specimens show no difference, and are ≤3.8.

The results show that through metabolization by BV-associated bacterial flora, the acid production from isomaltulose is faster than that from isomaltose and maltose, and especially faster than that from sucrose.

The normal vaginal pH value is generally in the range of 3.5 to 4.5, and the pH of vaginal secretions from BV patients is higher than 4.6. The growth of various bacteria has a most suitable pH range. When the pH is 5.4, the growth and metabolism to produce acids of neutrophilic bacteria are inhibited, while the acid resistant *Lactobacilli* and Bifidobacteria etc can still grow and produce acids. Therefore, the pH of a *Lactobacillus* selective medium is generally 5.4. Lactic acid is considered to play an important role in the maintenance of a normal vaginal bacterial flora, and protection against BV-associated bacterial flora and other pathogens[12]. In this example, the initial pH value of the carbohydrate containing gel is 5.4. Under such a pH condition, the carbohydrate is degraded by the BV-associated bacterial flora and primarily by the *Lactobacilli* among them, to produce acids. The faster the decline in the pH value of the gel is, the faster the inhibitory effect on harmful BV-associated bacteria is, and the faster the modulation for BV-associated bacterial flora will be.

It can be seen from the results of this example that the isomaltulose can be more easily degraded by BV-associated bacteria under slightly aerobic conditions to produce acids, so that isomaltulose is advantageous over isomaltose and maltose, and particularly obviously over sucrose. Therefore, isomaltulose is more suitable for use in the preparation of vaginal compositions according to the present invention.

Experimental Example 2

1. Experimental Purpose

To observe the promotion of isomaltulose for acid production by BV-associated bacteria, and compare the promotion effect with that of glucose, fructose, mannose, sucrose, maltose, and isomaltose.

2. Experimental Method (1) Grouping in experiment:
① Glucose group: containing 1.5% (w/v) glucose, MRS basal medium without carbohydrate, 5% (w/v) calf serum, and 0.45% (w/v) agar, pH5.4;
② Fructose group: containing 1.5% (w/v) fructose, MRS basal medium without carbohydrate, 5% (w/v) calf serum, and 0.45% (w/v) agar, pH5.4;
③ Mannose group: containing 1.5% (w/v) mannose, MRS basal medium without carbohydrate, 5% (w/v) calf serum, and 0.45% (w/v) agar, pH5.4;
④ Sucrose group: containing 1.5% (w/v) sucrose, MRS basal medium without carbohydrate, 5% (w/v) calf serum, and 0.45% (w/v) agar, pH5.4;
⑤ Maltose group: containing 1.5% (w/v) maltose, MRS basal medium without carbohydrate, 5% (w/v) calf serum, and 0.45% (w/v) agar, pH5.4;
⑥ Isomaltose group: containing 1.5% (w/v) isomaltose, MRS basal medium without carbohydrate, 5% (w/v) calf serum, and 0.45% (w/v) agar, pH5.4; and
⑦ Isomaltulose group: containing 1.5% (w/v) isomaltulose, MRS basal medium without carbohydrate, 5% (w/v) calf serum, and 0.45% (w/v) agar, pH5.4.

The semi-solid agar of each group was formulated essentially following the method described in Composition Example 1, then sterilized, added with calf serum, and packed in test tubes in a specification of 5 g/tube, for late use.

(2) Secretion specimens from BV patients: vaginal secretions from 5 BV patients; and the criteria of inclusion are:
① conforming to the Amsel clinical criteria of BV diagnosis, wherein the pH value of the vaginal secretions was >4.6;
② after smearing, Gram staining and microscopical examination of vaginal secretions, Nugent score ≥7; and
③ no other vaginosis and no antimicrobial agent is used within two weeks.

(3) After sampling, the secretion specimens from BV patients meeting the criteria of inclusion were immediately inoculated to the above 7 aseptic semi-solid agars containing a carbohydrate at the bedside and anaerobically incubated at 37° C. for 24 hrs. The pH values of the agar matrices are detected with a precise pH test paper.

3. Experimental Results

As shown in Table 2, after the secretion specimens from 5 BV patients are respectively anaerobically incubated for 24 hrs in 7 semi-solid agars containing a carbohydrate, the pH values of all the semi-solid agars decline from initial 5.4 to 3.8-4.6. From low to high, the pH values of isomaltulose and maltose are the lowest, followed by isomaltose, then sucrose, then glucose, and finally fructose and mannose.

TABLE 2

Effect of seven carbohydrates on acid production by BV-associated bacteria

| Specimen | 1 | 2 | 3 | 4 | 5 |
|---|---|---|---|---|---|
| Glucose | 4.1-4.4 | 4.1 | 3.8-4.1 | 3.8-4.1 | 3.8 |
| Fructose | 4.6 | 4.1 | 3.8-4.1 | 4.1 | 3.8 |
| Mannose | 4.4-4.6 | 4.4 | 3.8-4.1 | 4.1 | 3.8 |
| Sucrose | 4.1-4.4 | 3.8-4.1 | 3.8 | 4.1 | 3.8 |
| Maltose | 3.8 | 3.8 | 3.8 | 3.8 | 3.8 |
| Isomaltose | 3.8-4.1 | 4.1 | 3.8 | 3.8 | 3.8 |
| Isomaltulose | 3.8 | 3.8 | 3.8 | 3.8 | 3.8 |

4. Discussion

In this example, after the 7 semi-solid agars are inoculated with the secretion specimens from 5 BV patients respectively and anaerobically incubated for 24 hrs, the pH values in each culture tube decline. The magnitude of decline reflects the efficiency of acid production through metabolization of various carbohydrates by BV-associated bacteria under anaerobic conditions. In general, the decline in the pH value of a disaccharide containing semi-solid agar is greater than that of a monosaccharide containing semi-solid agar. Among the disaccharides, the isomaltulose and maltose containing semi-solid agars have a pH that declines more greatly than that of the sucrose and isomaltose containing semi-solid agars, indicating that in terms of the acid production through metabolization by BV-associated bacterial flora, disaccharide, particularly isomaltulose and maltose are faster than sucrose and isomaltose, and much faster than the monosaccharide.

The normal vaginal pH value is generally in the range of 3.5 to 4.5, and the pH of vaginal secretions from BV patients is higher than 4.6. The growth of various bacteria has a most suitable pH range. When the pH is 5.4, the growth and metabolism to produce acids of neutrophilic bacteria are inhibited, while the acid resistant *Lactobacilli* and Bifidobacteria etc can still grow and produce acids. Therefore, the pH of a *Lactobacillus* selective medium is generally 5.4. Lactic acid is considered to play an important role in the maintenance of a normal vaginal bacterial flora, and protection against BV-associated bacterial flora and other pathogens[12]. In this example, the initial pH value of the carbohydrate containing gel is 5.4. Under such a pH condition, the carbohydrate is degraded by the BV-associated bacterial flora and primarily by the *Lactobacilli* among them, to produce acids. The faster the decline in the pH value of the gel is, the faster the inhibitory effect on harmful BV-associated bacteria is, and the faster the modulation for BV-associated bacterial flora will be.

In summary, the results of this example show that isomaltulose is highly effectively in promoting the metabolism of vaginal bacterial flora to produce acids under anaerobic conditions, and is suitable for use in the preparation of vaginal compositions according to the present invention.

Experimental Example 3

1. Experimental Purpose

To observe the combined effect of isomaltulose and an antibacterial agent on acid production by BV-associated bacteria, and compare the effect with that of sucrose and isomaltose.

2, Experimental Method (1) Grouping in experiment:
① Sucrose-preservative group: containing 1.5% (w/v) sucrose, 0.5% (w/v) sodium propionate, 0.025% (w/v) sodium dehydroacetate, MRS basal medium without carbohydrate, 5% (w/v) calf serum, and 0.45% (w/v) agar, pH5.4;
② Isomaltose-preservative group: containing 1.5% (w/v) isomaltose, 0.5% (w/v) sodium propionate, 0.025% (w/v) sodium dehydroacetate, MRS basal medium without carbohydrate, 5% (w/v) calf serum, and 0.45% (w/v) agar, pH5.4;
③ Isomaltulose-preservative group: containing 1.5% (w/v) isomaltulose, 0.5% (w/v) sodium propionate, 0.025% (w/v) sodium dehydroacetate, MRS basal medium without carbohydrate, 5% (w/v) calf serum, and 0.45% (w/v) agar, pH5.4;
④ Sucrose control group: containing 1.5% (w/v) sucrose, MRS basal medium without carbohydrate, 5% (w/v) calf serum, and 0.45% (w/v) agar, pH5.4;
⑤ Isomaltose control group: containing 1.5% (w/v) isomaltose, MRS basal medium without carbohydrate, 5% (w/v) calf serum, and 0.45% (w/v) agar, pH5.4; and
⑥ Isomaltulose control group: containing 1.5% (w/v) isomaltulose, MRS basal medium without carbohydrate, 5% (w/v) calf serum, and 0.45% (w/v) agar, pH5.4.

The semi-solid agar of each group is formulated essentially following the method described in Composition Example 1, then sterilized, added with calf serum, and packed in test tubes in a specification of 5 g/tube, for late use.

(2) Secretion specimens from BV patients: vaginal secretions from 2 BV patients; and the criteria of inclusion are:
① conforming to the Amsel clinical criteria of BV diagnosis, wherein the pH value of the vaginal secretions was >4.6;
② after smearing, Gram staining, and microscopical examination of vaginal secretions, Nugent score ≥7; and
③ no other vaginosis, and no antimicrobial agent is used within two weeks.

(3) After sampling, the vaginal secretion specimens from BV patients meeting the criteria of inclusion were immediately inoculated to 3 semi-solid agars containing a carbohydrate and a preservative and 3 control agars at the bedside, and anaerobically incubated at 37° C. for 40 hrs. The pH values of the agar matrices are detected with a precise pH test paper after 30 or 32 hrs and 40 or 48 hrs of incubation.

3. Experimental Result

As shown in Table 3, after 30 or 32 hrs of incubation, the pH values of the control semi-solid agars without antibacterial agent decline to 3.8, or to 3.8-4.1.

After the semi-solid agars containing a carbohydrate and preservatives are anaerobically incubated for 30 or 32 hrs, the pH value of the semi-solid agar matrices declines, but is still higher than 4.4. After 40 or 48 hrs of incubation, the pH value of the 2 isomaltulose containing semi-solid agar matrices is below 4.1; the pH value of the 2 sucrose containing semi-solid agar matrices is 4.1 and 4.4 respectively; and the pH value of the 2 isomaltose containing semi-solid agar matrices is 4.4 and 4.6 respectively.

TABLE 3

Effect of carbohydrates and antibacterial agents in combination on acid production by BV-associated bacteria

| Specimen | Specimen 1 (30 hrs) | Specimen 1 (40 hrs) | Specimen 2 (32 hrs) | Specimen 2 (48 hrs) |
|---|---|---|---|---|
| Sucrose-antibacterial agent | 4.6 | 4.1 | 4.4-4.6 | 4.4 |
| Isomaltose-antibacterial agent | 4.6 | 4.4 | 4.6 | 4.6 |
| Isomaltulose-antibacterial agent | 4.4-4.6 | 3.8 | 4.4 | 3.8-4.1 |
| Sucrose control | 3.8 | | 3.8 | |
| Isomaltose control | 3.8 | | 3.8-4.1 | |
| Isomaltulose control | 3.8 | | 3.8 | |

4. Discussion

After the three semi-solid agars containing a carbohydrate and the same preservatives are inoculated with specimens from BV patients, and incubated for 30-48 hrs, the pH value of the agar matrix in the isomaltulose group is the lowest, and declines to 3.8 and 3.8-4.1 at 40 and 48 hrs, which are significantly lower than the values 4.1 and 4.4 of the sucrose group, and the values 4.4 and 4.6 of the isomaltose group.

The three control groups respectively contain 3 carbohydrates and no preservative. The pH of the agar matrices declines rapidly; and the pH value in 5 of 6 agar matrices declines to 3.8 at 30 and 32 hrs, and to 3.8-4.1 in 1 of 6 agar matrices, which are significantly lower than the pH of the preservative containing agar matrices, indicating that the preservatives have great influence on the acid production of the vaginal bacteria. The influence on the acid production through metabolization of sucrose and isomaltose by the vaginal bacteria is most prominent. The acid production is reduced, the pH of the matrices declines slowly, and the pH value in 3 of 4 agar matrices is still 4.4 or above at 40 and 48 hrs, and is 4.1 in 1 of 4 agar matrices. The isomaltulose is also influenced by the preservatives, but to a lesser extent. On one hand, the pH of the agar matrix containing isomaltulose can decline to 3.8 or 3.8-4.1 at 40 and 48 hrs, while excessive acid production and unduly reduction of pH are avoided. The results obtained in this example show that the isomaltulose is obviously advantageous over sucrose and isomaltose, and is more suitable for use in combination with preservatives in the preparation of vaginal compositions containing preservatives and/or antibacterial agents according to the present invention.

Experimental Example 4

1. Experimental Purpose

To observe the promotion of an isomaltulose gel for the growth of BV-associated bacteria, and compare the promotion effect with that of an isomaltose gel, a sucrose gel and a maltose gel.

2. Experimental Method (1) Grouping in experiment:
① Isomaltulose group: containing 1% (w/v) isomaltulose, MRS basal medium without carbohydrate, 5% (w/v) calf serum, and 0.5% (w/v) xanthan gum, pH5.4;
② Isomaltose group: containing 1% (w/v) isomaltose, MRS basal medium without carbohydrate, 5% (w/v) calf serum, and 0.5% (w/v) xanthan gum, pH5.4;
③ Sucrose group: containing 1% (w/v) sucrose, MRS basal medium without carbohydrate, 5% (w/v) calf serum, and 0.5% (w/v) xanthan gum, pH5.4; and
④ Maltose group: containing 1% (w/v) maltose, MRS basal medium without carbohydrate, 5% (w/v) calf serum, and 0.5% (w/v) xanthan gum, pH5.4.

The gel of each group was formulated essentially following the method described in Composition Example 1, then sterilized, added with calf serum, and packed in test tubes in a specification of 5 g/tube, for late use.

(2) Secretion specimens from BV patients: vaginal secretions from 20 BV patients; and the criteria of inclusion are:
① conforming to the Amsel clinical criteria of BV diagnosis;
② after smearing, Gram staining and microscopical examination of vaginal secretions, Nugent score ≥7; and
③ no other vaginosis and no antimicrobial agent is used within two weeks.

(3) After sampling, the vaginal secretion specimens from BV patients meeting the criteria of inclusion were immediately inoculated to the above 4 gels containing a carbohydrate, slightly aerobically incubated at 37° C. for 48 hrs, then transferred to a plate containing improved MRS with 1% (w/v) glucose and 5% (w/v) calf serum, slightly aerobically incubated for 20-48 hrs, isolated, purified and multiplied. The strain was identified by 16s rDNA sequencing.

3. Experimental Result (1) As shown in Table 4, after the vaginal secretions from BV patients are incubated with 4 carbohydrate containing gels respectively, with the isomaltulose, isomaltose and sucrose gels, *Lactobacilli* are cultured from the secretions derived from 9 BV patients; and with the maltose gel, *Lactobacilli* are cultured from the secretions derived from 8 BV patients, wherein no *L. iners* is cultured. For the secretions derived from 9 BV patients from which *Lactobacilli* are cultured, there are 4 cases of *L. jensenii,* 2 cases of *L. gasseri* and each 1 case of *L. crispatus, L. mucosae* and *L. amylovorus*. This indicates that the 4 carbohydrate containing gels have a potent promotion for the growth of *L. jensenii, L. gasseri* and *L. crispatus,* and a weak promotion for the growth of *L. iners*.

TABLE 4

Selective promotion of 4 carbohydrate containing gels for the growth of Lactobacilli in the secretions from BV patients

|  | Isomaltulose | Isomaltose | Sucrose | Maltose |
|---|---|---|---|---|
| *L. jensenii* | 4[1] (3[2], 4, 11, 18) | 4 (3, 4, 11, 18) | 4 (3, 4, 11, 18) | 3 (4, 11, 18) |
| *L. gasseri* | 2 (1, 20) | 2 (1, 20) | 2 (1, 20) | 2 (1, 20) |

TABLE 4-continued

Selective promotion of 4 carbohydrate containing gels for the growth of Lactobacilli in the secretions from BV patients

|  | Isomaltulose | Isomaltose | Sucrose | Maltose |
|---|---|---|---|---|
| L. crispatus | 1 (15) | 1 (15) | 1 (15) | 1 (15) |
| L. iners | 0 | 0 | 0 | 0 |
| L. mucosae | 1 (4) | 1 (4) | 1 (4) | 1 (4) |
| L. amylovorus | 1 (9) | 1 (9) | 1 (9) | 1 (9) |
| In total | 9 | 9 | 9 | 8 |

Note 1:
the FIG. "4" refers to the total number of samples positive for L. jensenii incubation, the same in Tables 2, and 3; and
Note 2:
the figure in the parenthesis refers to the numbering of samples positive for L. jensenii incubation, the same in Tables 2, and 3.

(2) As shown in Table 5, after the vaginal secretions from BV patients are incubated with 4 carbohydrate containing gels respectively, *Bifidobacterium bifidum* is only cultured from the secretion derived from 1 BV patient with the maltose gel, and no *Bifidobacterium breve*, *Bifidobacterium dentium* and *Bifidobacterium longum* is cultured from the remaining 3 gels, suggesting that the gels containing isomaltulose, isomaltose, and sucrose as a carbohydrate have a weak promotion for the growth of Bifidobacteria commonly found in BV-associated flora.

TABLE 5

Selective promotion of 4 carbohydrate containing gels for the growth of Bifidobacteria in the secretions from BV patients

|  | Isomaltulose | Isomaltose | Sucrose | Maltose |
|---|---|---|---|---|
| Bifidobacterium bifidum | 0 | 0 | 0 | 1 (8) |
| Bifidobacterium breve | 0 | 0 | 0 | 0 |
| Bifidobacterium dentium | 0 | 0 | 0 | 0 |
| Bifidobacterium longum | 0 | 0 | 0 | 0 |
| In total | 0 | 0 | 0 | 1 |

(3) As shown in Table 6, after the vaginal secretions from BV patients are incubated with 4 carbohydrate containing gels respectively, *Gardnerella vaginalis* is cultured from the secretions of 6 BV patients with the maltose gel, from the secretions derived from 3 BV patients with the sucrose gel, and from the secretions derived from 2 BV patients with the isomaltulose and isomaltose gels, suggesting that the maltose gel facilitates the growth of *Gardnerella vaginalis*.

TABLE 6

Selective promotion of 4 carbohydrate containing gels for the growth of Gardnerella vaginalis in the secretions from BV patients

|  | Isomaltulose | Isomaltose | Sucrose | Maltose |
|---|---|---|---|---|
| Gardnerella vaginalis | 2 (15, 19) | 2 (15, 19) | 3 (8, 15, 19) | 6 (2, 6, 7, 9, 15, 19) |
| In total | 2 | 2 | 3 | 6 |

4. Discussion

Relevant studies[4] have found that the BV-associated bacterial flora is complex, and contains *Gardnerella vaginalis*, *Prevotella*, *Megacoccus*, *Mobiluncus*, *Peptostreptococcus*, *Finegoldia*, *Anaerococcus*, and *Sneathia* as preponderant bacteria, wherein the copies of 16S rRNA gene sequence of *Gardnerella vaginalis* rank first and account for 29.1% of the total copies of 16S rRNA gene sequences of the bacterial flora in the BV patients, which are over two times of the copies of 16S rRNA gene sequence of *Prevotella* that come in second (13.2%), and three times of the copies of 16S rRNA gene sequence of *Megasphaera* that are in the third place (9.8%). For the moderate BV, the copies of 16S rRNA gene sequence of *Gardnerella vaginalis* account for 30.5% of the total copies of 16S rRNA gene sequences of the vaginal bacterial flora in the patients with moderate BV, and are second to *L. iners*. It can be seen that *Gardnerella vaginalis* is one of the most representative preponderant bacteria in the vaginal bacterial flora of BV patients.

The *Lactobacilli* in the BV-associated bacterial flora are reduced. The copies of 16S rRNA gene sequence of *L. iners* account for 6.6% of the total copies of 16S rRNA gene sequences of the bacterial flora in the BV patients and are in the sixth place; the value is only 0.3% for *L. crispatus*; and the value is even lower for *L. jensenii* and *L. gasseri*, which plus the value for other species of *Lactobacilli* is only 0.2% in total. For the moderate BV, the copies of 16S rRNA gene sequence of *L. iners* rank first and account for 43.9% of the total copies of 16S rRNA gene sequences of the vaginal bacterial flora, the value for *L. crispatus* is 1.2%, and the value for *L. jensenii*, *L. gasseri* and other *Lactobacilli* is 6.1% in total.

In this example, after the vaginal secretions from 20 typical BV patients are incubated with 4 carbohydrate containing gels, the *Lactobacilli* are cultured from the secretions of 9 BV patients with the isomaltulose, isomaltose and sucrose gels, and from the secretions of 8 BV patients with the maltose gel. The species of the cultured *Lactobacilli* are primarily *L. jensenii*, and *L. gasseri* rarely found in the BV-associated bacterial flora, and secondarily *L. crispatus*, *L. mucosae* and *L. amylovorus* rarely found in the BV-associated bacterial flora. However, *L. iners* which is most frequently found in the BV-associated bacterial flora does not grow. These suggest that the gels containing isomaltulose, isomaltose, sucrose, and maltose are selective for the *Lactobacilli* in the secretions from the BV patients, and have a potent promotion effect for the growth of *L. jensenii*, *L. gasseri*, and *L. crispatus*, and a weak promotion effect for the growth of *L. iners*.

In the BV-associated bacterial flora, *Gardnerella vaginalis* is the most prevelant. In this example, *Gardnerella vaginalis* is cultured from the secretions of 6 BV patients with the maltose gel, from the secretions of 3 BV patients with the sucrose gel, and from the secretions of 2 BV patients with the isomaltulose and isomaltose gels, suggesting that the maltose gel is more suitable for the growth of *Gardnerella vaginalis*, and the isomaltulose and isomaltose gels are relatively not suitable for the growth of *Gardnerella vaginalis*.

The Bifidobacteria in the BV-associated bacterial flora are mostly *Bifidobacterium bifidum*, *Bifidobacterium breve*, *Bifidobacterium dentium*, and *Bifidobacterium longum*. In this example, *Bifidobacterium bifidum* is cultured only from the secretion of 1 BV patient with the maltose gel, and no Bifidobacteria grows with the isomaltulose, isomaltose and sucrose gels, suggesting that the isomaltulose, isomaltose, and sucrose have no effect of promoting the growth of Bifidobacteria in the secretions of BV patients.

5. Conclusion the isomaltulose, isomaltose, sucrose and maltose gels can all selectively promote the growth of *L. jensenii, L. gasseri, L. crispatus, L. mucosae* and *L. amylovorus* in the secretions of BV patients, but have no obvious promotion effect for the growth of *L. iners*.

The isomaltulose, isomaltose and sucrose gels have no obvious promotion effect for the growth of Bifidobacteria in the secretions of BV patients.

The maltose gel may have a promotion effect for the growth of *Gardnerella vaginalis* in the vaginal secretions of BV patients, and the promotion effect of the isomaltulose and isomaltose gels for the growth of *Gardnerella vaginalis* is not obvious.

In summary, the study results in this example suggest that in modulation of the bacterial flora, the isomaltulose is advantageous over maltose, and is more suitable for use in the preparation of vaginal compositions according to the present invention.

Experimental Example 5

1. Experimental Purpose to investigate the metabolization of isomaltulose by *Canidia albicans*, and compare the metabolization with that of isomaltose, sucrose and maltose.

2. Experimental Method (1) Grouping in experiment:
Isomaltulose group: containing 1.5% (w/v) isomaltulose, MRS basal medium without carbohydrate, and 5% (w/v) calf serum, pH 7.0;
Isomaltose group: containing 1.5% (w/v) isomaltose, MRS basal medium without carbohydrate, and 5% (w/v) calf serum, pH 7.0;
Sucrose group: containing 1.5% (w/v) sucrose, MRS basal medium without carbohydrate, and 5% (w/v) calf serum, pH 7.0; and
Maltose group: containing 1.5% (w/v) maltose, MRS basal medium without carbohydrate, and 5% (w/v) calf serum, pH7.0.

The culture medium of each group was strictly aseptically formulated, and packed in test tubes in a specification of 5 g/tube, for late use.

(2) Test strain: 2 strains of *Canidia albicans*, isolated from patients with candidal vaginitis.

(3) The bacterial solutions containing 2 strains of *Canidia albicans* were aseptically inoculated into each test tube, aerobically incubated at 37° C. for 72 hrs, and sterilized at 80° C. for 30 min. The supernatant was separated by centrifugation, and packed in a specification of 5 ml/tube. The carbohydrate content in each tube was detected by HPLC.

3. Experimental Result

As shown in Table 7, after the *Canidia albicans* is incubated for 72 hrs with culture media containing 1.5% (w/v) isomaltulose, isomaltose, sucrose and maltose respectively, the concentrations of the four carbohydrate decrease to different degrees, and the magnitude of decrease is noted in the sequence of maltose, isomaltulose, isomaltose and sucrose. The maltose is decreased from 1.5% (w/v) to below 0.05% (w/v).

TABLE 7

Metabolization of four carbohydrates by *Canidia albicans*

|  | Isomaltulose (g %) | Isomaltose (g %) | Sucrose (g %) | Maltose (g %) |
|---|---|---|---|---|
| *Canidia albicans* 1 | 0.11 | 0.74 | 1.04 | Not detected[1] |
| *Canidia albicans* 2 | 0.12 | 0.76 | 0.95 | Not detected |

Note[1]:
The detection limit is 0.05% (w/v).

4. Discussion

According to the report in relevant literatures, 85% or more of the pathogens associated with candidal vaginitis is *Canidia albicans*. After the two strains of *Canidia albicans* are incubated for 72 hrs with the 4 carbohydrate containing culture media respectively, the residual concentration of maltose is below 0.05% (w/v) for both strains, the residual concentration of isomaltulose is 0.11% (w/v) for one strain and 0.12% (w/v) for the other stain, the residual concentration of isomaltose is 0.74% (w/v) for one strain and 0.76% (w/v) for the other stain, and the residual concentration of sucrose is the highest, and is 1.04% (w/v) for one strain and 0.95% (w/v) for the other stain. These suggest that the four carbohydrates can all be metabolized by *Canidia albicans*, wherein the metabolization capability is relatively highest for maltose, and relatively the lowest for sucrose. It can be seen from the study results in this example that the sucrose, isomaltose and isomaltulose are advantageous over maltose, and are more suitable for use in the preparation of vaginal compositions according to the present invention.

Experimental Example 6

1. Experimental Purpose

To observe the combined effect of isomaltulose and preservatives on the growth of BV-associated bacteria.

2. Experimental Method (1) isomaltulose agar: 1.5% (w/v) isomaltulose, 0.05% (w/v) sodium benzoate, 0.5% (w/v) sodium propionate, 0.025% (w/v) sodium dehydroacetate, MRS basal medium without carbohydrate, 5% (w/v) calf serum, and 0.45% (w/v) agar, pH 5.4.

The composition was formulated essentially following the method of Composition Example 1, then sterilized, added with calf serum, and packed in test tubes in a specification of 5 g/tube, for late use.

(2) Secretion specimens of BV patients: vaginal secretions from 1 BV patients; and criteria of inclusion:
① conforming to the Amsel clinical criteria of BV diagnosis, wherein the pH of the vaginal secretions was >4.6;
② after smearing, Gram staining, and microscopical examination of vaginal secretions, Nugent score ≥7; and
③ no other vaginosis, and no antimicrobial agent is used within two weeks.

(3) After being sampled by a vaginal swab, the vaginal secretion specimens from a BV patient meeting the criteria of inclusion were washed off into a MRS basal medium without carbohydrate at bed side, immediately inoculated to the isomaltulose agar, and anaerobically incubated at 37° C. for 40 hrs. The agar matrix and the secretion specimen as a solution were shipped to Sangon Biotech (Shanghai) Co., Ltd., for 16s rDNA metagenome sequencing, and detecting the *Lactobacillus*, *L. crispatus*, *L. iners*, *L. jensenii*, *L. gasseri*, *Gardnerella vaginalis* and *Prevotella* by qPCR.

3. Experimental Result (1) As shown in Table 8, the bacteria in the vaginal secretions of this BV patient have *Sneathia* (43.02%), *Prevotella* (19.44%) and *Gardnerella* (12.68%) as preponderant bacteria. After inoculation to the isomaltulose agar and anaerobic incubation for 40 hrs, the *Lactobacilli* account for 91%, and the *Gardnerella vaginalis* accounts for 6%.

(2) As shown in Table 9, the DNA copies listed therein are respectively the bacterial DNA copies contained in 0.12 ml of agar matrix and 0.12 specimen suspension. It is found through detection of 7 bacteria in the secretion specimen of the BV patient by qPCR that the number of the *Prevotella* and *Gardnerella vaginalis* is large; the number of the *Lactobacillus*, *L. crispatus* and *L. iners* is rare, the number of *L. jensenii* is extremely rare, and no *L. gasseri* is detected. It is found through detection of 7 bacteria in the isomaltulose agar by qPCR that the number of *L. crispatus* is the most prevelant, the number of *L. jensenii* is rare, and no *L. gasseri* is detected. The number of the *L. iners* and *Prevotella* is reduced and the number of the *Gardnerella vaginalis* is increased.

TABLE 8

Effect of isomaltulose and antibacterial agents in combination on the growth of BV-associated bacteria

| Genus and species of bacteria | Vaginal secretion of BV patients (%) | Isomaltulose-antibacterial agent gel (%) |
|---|---|---|
| Lactobacillus | 0.82 | 90.59 |
| Gardnerella | 12.68 | 6.41 |
| Streptococcus | 0.13 | 0.07 |

TABLE 8-continued

Effect of isomaltulose and antibacterial agents in combination on the growth of BV-associated bacteria

| Genus and species of bacteria | Vaginal secretion of BV patients (%) | Isomaltulose-antibacterial agent gel (%) |
|---|---|---|
| Veillonella | 0.07 | 0.01 |
| Peptostreptococcus | 0.13 | 0 |
| Clostridium sensu stricto | 0 | 0 |
| Sneathia | 43.02 | 0.47 |
| Prevotella | 19.44 | 0.29 |
| Aerococcus | 0.01 | 0.37 |
| Atopobium | 3.94 | 0.04 |
| Dialister | 0.59 | 0.14 |
| Saccharofermentans* | 9.26 | 0.08 |
| Actinomyces | 0 | 0.25 |
| Finegoldia | 0 | 0.44 |
| Megasphaera | 3.36 | 0.07 |
| Parvimonas* | 1.3 | 0.07 |
| Enterorhabdus* | 0.63 | 0.03 |
| Others | 4.59 | 0.5 |
| In total | 100 | 100 |

*Temporarily no Chinese name

TABLE 9

Effect of isomaltulose on the growth of BV-associated bacteria

| | Lactobacillus | L. iners | L. crispatus | L. jensenii | L. gasseri | Gardnerella vaginalis | Prevotella |
|---|---|---|---|---|---|---|---|
| Bacterial DNA copies in specimen of BV patient | 372946 | 56296 | 2355 | 3.2 | — | 4214328 | 14866667 |
| Bacterial DNA copies in isomaltulose agar | 275033167 | 33167 | 889000000 | 12.2 | — | 18000000 | 911000 |

4. Discussion

The experimental results show that after the BV-associated bacteria are anaerobically incubated for 40 hrs in the isomaltulose agar containing antibacterial agents, the metagenome sequencing shows that *Lactobacilli* grow largely and become preponderant bacteria, while the proportion of *Sneathia*, *Prevotella* and *Gardnerella* in the flora decreases greatly. Further detection by qPCR confirms that the preponderant *Lactobacilli* are *L. crispatus*, the copies of the DNA sequence of which are increased by 377494 times, from 2355 to 889000000. However, the copies of the DNA sequence of *L. iners* are reduced from 56296 to 33167. The number of *Prevotella* is reduced, and the number of *L. jensenii* is still very small. It is noted that the copies of the DNA sequence of *L. crispatus* are more than the copies of the DNA sequence of *Lactobacillus*, which may be attributed to that the bacteria amplified with the primer for *Lactobacillus* do not include all the bacteria belonging to the genus, and that the bacteria amplified with the primer for *L. crispatus* do not exclusively include *L. crispatus*, as supposed after discussion with the specialist from Sangon Biotech (Shanghai) Co., Ltd. The absolute number of *Gard-* nerella vaginalis is also increased by 4.27 times, which may be correlated with the ability to support the growth of Gardnerella vaginalis by the calf serum contained in the agar matrix.

The results obtained in this example show that the isomaltulose has a notable promotion effect for the growth of protective L. crispatus, and not for the growth of L. iners, suggesting that the isomaltulose and antibacterial agents in combination are suitable for the preparation of compositions according to the present invention.

Experimental Example 7

1. Experimental Purpose

To observe the antibacterial effect of different preservatives on the Candida and Lactobacilli.

2. Experimental Method (1) Preparation of culture media containing different preservatives The following culture media containing different concentrations of preservatives were formulated with a basal medium containing 0.5% (w/v) isomaltulose, MRS medium without carbohydrate, and 5% (w/v) calf serum:

A. 0.1% (w/v) sodium benzoate
B. 0.2% (w/v) sodium benzoate
C. 0.02% (w/v) sodium dehydroacetate
D. 0.25% (w/v) sodium propionate group
E. 0.5% (w/v) sodium propionate group
F. 0.02% (w/v) sodium dehydroacetate+0.25% (w/v) sodium propionate group
G. 0.02% (w/v) sodium dehydroacetate+0.5% (w/v) sodium propionate group The culture medium of each group was adjusted to pH 5.4, sterilized and packed in a test tube in a specification of 2 ml/tube.

(2) Inoculation and incubation of test strains: a bacterial suspension containing $(1-5) \times 10^5$ cfu/ml Candida glabrada isolate and a bacterial suspension containing $(1-5) \times 10^5$ cfu/ml L. jensenii were inoculated to each tube respectively. The Candida glabrada was aerobically incubated at 37° C. for 72 hrs, and the L. jensenii was microaerophilic incubated for 22 hrs.

(3) Observations: the turbidity in the L. jensenii incubation tube was observed at 22 hrs, and the turbidity in the Candida glabrada incubation tube was observed at 72 hrs.

3. Test results

As shown in Table 10, 0.1% (w/v) sodium benzoate has a potent inhibition on Lactobacilli, and can fully inhibit the growth of Lactobacilli at 22 hrs. 0.02% (w/v) sodium dehydroacetate and 0.5% (w/v) sodium propionate has a weak inhibition on Lactobacilli, as indicated by a greatly increased turbidity of Lactobacilli at 22 hrs.

When used alone, 0.2% (w/v) sodium benzoate, 0.02% (w/v) sodium dehydroacetate, and 0.5% (w/v) sodium propionate show a weak inhibition on Candida glabrada, as indicated by a greatly increased turbidity of Candida glabrada at 72 hrs.

The sodium dehydroacetate and sodium propionate have a synergistic inhibition on Candida glabrada. When 0.02% (w/v) sodium dehydroacetate and 0.5% (w/v) sodium propionate are used in combination, the growth of Candida glabrada can be completely inhibited at 72 hrs, with the turbidity being unchanged. However, the inhibition on L. jensenii is relatively weak, and the turbidity is increased at 22 hrs.

TABLE 10

Effect of isomaltulose and preservatives in combination on the growth of vaginal bacteria from BV patients

|  | 0.1% sodium benzoate | 0.2% sodium benzoate | 0.02% sodium dehydroacetate | 0.25% sodium propionate | 0.5% sodium propionate | 0.02% sodium dehydroacetate 0.25% sodium propionate | 0.02% sodium dehydroacetate 0.5% sodium propionate |
|---|---|---|---|---|---|---|---|
| Lactobacilli (0 hr) | 0.6 | 0.7 | 0.5 | 0.6 | 0.4 | 0.5 | 0.4 |
| Lactobacilli (22 hrs) | 0.9 | 0.7 | 1.4 | 5.2 | 1.7 | 1.4 | 0.7 |
| Candida (0 hr) | 0.6 | 0.6 | 0.5 | 0.5 | 0.4 | 0.4 | 0.2 |
| Candida (72 hrs) | 7.1 | 2.1 | 3.9 | >7.5 | 6.3 | 2.6 | 0.2 |

*: The concentration in Table 10 is in "w/v".

4. Conclusion

The results obtained in this experimental example confirm that when used in combination, 0.02% (w/v) sodium dehydroacetate and 0.5% (w/v) sodium propionate has a higher inhibitive effect on Candida glabrada than that of 0.2% (w/v) sodium benzoate.

When used in combination, 0.02% (w/v) sodium dehydroacetate and 0.5% (w/v) sodium propionate has a weaker inhibitive effect on L. jensenii than that of 0.2% (w/v) sodium benzoate.

Experimental Example 8

Two female rhesus monkeys were screened. The vaginal secretions of them had a pH value of 5.1 and 4.8 respectively, the vaginal bacteria were primarily Gram negative bacilli and Gram positive cocci, no gross Gram positive bacilli were found, and the white cells were rare. 0.5 g of the isomaltulose gel obtained in Composition Example 1 was dosed once a day for 5 consecutive days. Upon reexamination, the vaginal pH values were 3.8 and 4.1 respectively, and the vaginal bacteria were primarily gross Gram positive bacilli.

Experimental Example 9

Female, 28 years old, healthy, without unwell feeling, and had regular menstrual cycle. The vaginal secretions were removed with a vaginal swab 3 days after the completion of the menstrual cycle, and were tested to have a pH of 4.8. After smearing, Gram staining, and microscopical examination, more gross Gram positive bacilli, some Gram positive cocci, a few Gram negative bacilli, and rare white cells were found. The woman voluntarily received the composition prepared in Composition Example 2 for vaginal cleaning and nursing, in a dosage of 3 g each application, for consecutive 2 days. The vaginal secretions were removed again with a vaginal swab, and were tested to have a pH of 4.1. After smearing, Gram staining, and microscopical examination, more gross Gram positive bacilli were found, and the Gram positive cocci and negative bacilli were reduced. The woman had a cleaner, comfortable, and refreshing feeling in the vagina.

Experimental Example 10

Female, 52 years old, over 1 year after menopause, and often had a feeling of vaginal dryness and occasionally slight sting. The vaginal secretions were removed with a vaginal swab, and were tested to have a of pH 5.1. After smearing, Gram staining, and microscopical examination, it was found that few bacteria were present, which are mostly Gram positive cocci, occasionally Gram positive bacilli, and rarely white cells. The woman voluntarily received the composition prepared in Composition Example 13 for vaginal cleaning and nursing, in a dosage of 5 g each application, for consecutive 5 days. The vaginal secretions were removed again with a vaginal swab, and were tested to have a of pH 4.1. After smearing, Gram staining, and microscopical examination, more gross Gram positive bacilli were found, while other types of bacteria are few. The woman had a feeling of comfort and no dryness and sting in the vagina.

Experimental Example 11

Female, 35 years old, diagnosed of "vaginitis" in the hospital due to leukorrhagia and odor of leucorrhea, received treatment with "Shuangzuotaishuan" comprising metronidazole, clotrimazole and chlorhexidine acetate, once a day for 5 consecutive days, and found that the leucorrhea was reduced and the odor disappeared. The vaginal secretions were removed with a vaginal swab, and tested to have a pH of 5.4. After smearing, Gram staining and microscopical examination, it was found that few bacteria were present, and no white cell was found. The woman voluntarily received the composition prepared in Composition Example 6 for vaginal cleaning and nursing, once a day in a dosage of 5 g each application, for consecutive 3 days. The vaginal secretions were removed again with a vaginal swab, and were tested to have a pH of 3.8. After smearing, Gram staining, and microscopical examination, more gross Gram positive bacilli were found. The woman had a feeling of comfort and ease.

Experimental Example 12

Female, 41 years old, with suspected "vaginal dysbacteriosis" from smear examination of vaginal secretion upon physical examination, but having no obvious discomfort usually. The vaginal secretions were removed with a vaginal swab, and were tested to have a pH of 4.6. After smearing, Gram staining, and microscopical examination, fewer gross Gram positive bacilli and more Gram positive cocci were found, small Gram-variable bacilli were found, the Nugent score was 5, and there were few white cells, which conformed to the manifestation of moderate BV. The woman voluntarily received the composition prepared in Composition Example 17 for vaginal cleaning and nursing, once a day in a dosage of 5 g each application, for consecutive 5 days. Upon reexamination, the pH value of the vaginal secretion was 3.8, the vaginal bacteria were primarily gross Gram positive bacilli. Gram positive cocci and small Gram negative bacilli were considerably reduced. The woman had a feeling of clean leucorrhea and freshness.

Experimental Example 13

Female, 45 years old, with repeatedly reoccurring leukorrhagia accompanied by pruritus, wherein the symptoms were alleviated or disappeared after treatment with antibacterial agents, but often reoccurred after menstruation. The vaginal secretions were removed with a vaginal swab, and were tested to have a pH of 5.4. After smearing, Gram staining and microscopical examination, it was found that the gross Gram positive bacilli were rare, the bacteria were primarily a variety of Gram negative bacilli, Gram negative cocci and Gram positive cocci, and the white cells were few, which conformed to the manifestation of bacterial vaginosis. The woman voluntarily received the composition prepared in Composition Example 21 for vaginal cleaning and nursing, once a day in a dosage of 1 tablet each application, for consecutive 5 days. Upon reexamination, the pH value of the vaginal secretion was 4.1, the vaginal bacteria were primarily gross Gram positive bacilli. Gram negative bacilli, negative cocci and positive bacilli were considerably reduced. The woman felt no discomfort.

REFERENCES

1. Rita Verhelst, Hans Verstraelen, Geert Claeys, et al. Comparison between Gram stain and culture for the characterization of vaginal microflora: Definition of a distinct grade that resembles grade I microflora and revised categorization of grade I microflora. BMC Microbiology 2005, 561. Dol: 10.1186/1471-2180-5/61
2. Zhou X, Bent S J, Schneider M G, et al. Characterization of vaginal microbial communities in adult healthy women using cultivation-independent methods. Microbiology, 2004, 150: 2565-2573.
3. Linhares I M, Giraldo P C, Baracat E C. New findings about vaginal bacterial flora. Rev Assoc Med Bras, 2010, 56(3): 370-374.
4. Rampersaud R, Randis T M, Ratner A J, et al. Microbiota of the upper and lower genital tract. Semin Fetal Neonatal Med, 2012, 17(1): 51-57.
5. Fredricks D N, Fiedler T L, Marrazzo J M. Molecular identification of bacteria associated with bacterial vaginosis. N Engl J Med, 2005, 353: 1899-1911.
6. M. WILKS, Soad Tabaqchali. Quantitative bacteriology of the vaginal flora during the menstrual cycle. J. Med. Microbiol, Vol. 24(1987), 241-245.
7. Tevi-Benissan C, Belec L, Levy M, et al. In vivosemen associated pH neutral-lization of cervicovaginal secretions. Clin Diagn Lab Immunol 1997; 4: 367-74.
8. Jenny L. Martino and Sten H. Vermund. Vaginal Douching: Evidence for Risks or Benefits to Women's Health. Epidemiologic Reviews 2002; 24:109-124.
9. Livengood C H. Bacterial vaginosis: an overview for 2009. Rev Obstet Gynecol, 2009, 2(1): 28-37.
10. Livengood C H 3nd, Ferris D G, Wiesenfeld H C et al. Effectveness of two tinidazole regimens in treatment of bacterial vaginosis: a randomized controlled trial. Obstet Gynecol. 2007; 110: 302-309.
11. Thomas K K, Sanchez S, Garcia P J et al. Why do different criteria for 'cure' yield different conclusions in comparing two treatments for bacterial vaginosis? Ser Transm Dis. 2005; 32: 526-530.
12. Ma B, Forney L J, Ravel J. Vaginal microbiome rethinking health and disease. Annu Rev Microbiol. 2012; 66: 371-89
13. Antonio M A, Hawes S E, Hillier S L. The identification of vaginal *Lactobacillus* species and the demographic and microbiologic characteristics of women colonized by these species. J Infect Dis, 1999; 180: 1950-6.
14. Shipitsyna E, Roos A, Datcu R, et al. Composition Of The Vaginal Microbiota In Women of Reproductive Age-Sensitive And Specific Molecular Diagnosis Of Bacterial Vaginosis Is Possible? PLoS ONE 8(4): e60670.Doi: 10.1371/pone.0060670.

What is claimed is:

1. A vaginal composition, comprising:
   (1) isomaltulose, and
   (2) antibacterial agents comprising: propionic acid and/or sodium propionate, and dehydroacetic acid and/or sodium dehydroacetate,
   wherein the content of the isomaltulose is 0.05 to 20.0% (w/w), and the content of the antibacterial agents is 0.05 to 2.5% (w/w) in total.

2. The composition according to claim 1, wherein the content of the isomaltulose is 1.5 to 12.0% (w/w).

3. The composition according to claim 1, wherein the composition further comprises 0.001 to 1.0% (w/w) in total of an estrogen and/or phytoestrogen.

4. The composition according to claim 3, wherein the estrogen and/or phytoestrogen is selected from the group consisting of: stilboestrol, estradiol, estriol, daidzin, daidzein, genistin, genistein, glycitin, glycitein, biochanin A, coumestrol and formononetin, and a combination thereof.

5. The composition according to claim 1, wherein the composition is formed as one of the following: non-therapeutic vaginal health products, vaginal commodities, vaginal health care products, vaginal care products, vaginal cosmetics, vaginal hygiene products, or vaginal cleaning products; therapeutic vaginal health products, vaginal medical devices, or vaginal medicines; or vaginal cleaning agents or nourishing agents, deodorants, antipruritic agents, fresheners, wetting agents, lubricating agents, disinfectants, antibacterial agents, topical microbicidal agents, microecological modulators, or microorganism regulating agents.

6. The composition according to claim 1, wherein the composition further comprises one or more extracts and vitamins selected from the group consisting of 0.1 to 5.0% (w/w) of aloe extract, 0.1 to 5.0% (w/w) of lavender extract, 0.001 to 1.0% (w/w) of vitamin E, 0.001 to 1.0% (w/w) of vitamin A, 0.001 to 1.0% (w/w) of vitamin D, 0.001 to 1.0% (w/w) of vitamin C, or a combination thereof.

7. The composition according to claim 1, wherein the composition is a non-flowable, viscous water-soluble gel, which further comprises: a non-flowable, viscous water-soluble gel matrix, wherein the gel matrix is xanthan gum or Carbomer,
   wherein the content of the isomaltulose is 0.1 to 20% (w/v);
   and the content of the antibacterial agents, in total, is 0.1 to 2.5% (w/v);
   wherein the antibacterial agents further comprise one or more agents selected from a group consisting of benzoic acid, sodium benzoate, sorbic acid, potassium sorbate, sodium sorbate, acetic acid, sodium acetate, diacetic acid, sodium diacetate, calcium propionate, caprylic acid, sodium caprylate, capric acid, sodium caprate, undecylenic acid, sodium undecylenate, lauric acid, sodium laurate, natamycin, lactoferrin, lactoferricin, and a combination thereof; and
   wherein the pH value of the water-soluble gel is 3.5 to 6.0.

8. The composition according to claim 7, wherein the content of the isomaltulose is 3.0 to 12.0% (w/v).

9. The composition according to claim 1, wherein the composition is in vaginal dosage forms comprising: water-soluble gels, aqueous solutions, aerosols, creams, ointments, capsules, microcapsules, suppositories, effervescents, or tablets.

* * * * *